United States Patent [19]

Lautenschläger

[11] Patent Number: 5,044,371
[45] Date of Patent: Sep. 3, 1991

[54] MEMORY UNIT FOR CONTROLLING AN ERGOMETER

[75] Inventor: Peter Lautenschläger, Gonbach, Fed. Rep. of Germany

[73] Assignee: Keiper Dynavit GmbH & Co., Fed. Rep. of Germany

[21] Appl. No.: 493,749

[22] Filed: Mar. 15, 1990

[30] Foreign Application Priority Data

Mar. 17, 1989 [DE] Fed. Rep. of Germany ....... 3908756

[51] Int. Cl.⁵ .............................................. A61B 5/04
[52] U.S. Cl. .................................. 128/707; 364/413.04
[58] Field of Search ..................... 128/707, 706, 710; 364/413.02, 413.03, 413.04

[56] References Cited

U.S. PATENT DOCUMENTS

| | | | |
|---|---|---|---|
| 3,845,756 | 11/1974 | Olsson | 128/707 |
| 4,112,928 | 9/1978 | Putsch | 128/707 |
| 4,278,095 | 7/1981 | Lapeyre | 128/689 |
| 4,281,663 | 8/1981 | Pringle | 128/707 |
| 4,436,097 | 3/1984 | Cunningham | 128/707 |
| 4,649,930 | 3/1987 | Groch et al. | 128/706 |

Primary Examiner—Francis Jaworski
Assistant Examiner—George Manuel
Attorney, Agent, or Firm—Wigman & Cohen

[57] ABSTRACT

A memory unit for the non-volatile storage of data for controlling an ergometer with respect to the performance applied by the user in dependence on time and/or distance is formed as an independent structural unit which can be connected by the user to an ergometer for a selectable period of time for data recording and/or data reading.

28 Claims, 2 Drawing Sheets

MEMORY UNIT FOR CONTROLLING AN ERGOMETER

BACKGROUND OF THE INVENTION

The present invention relates to a memory unit for the permanent storage of data for controlling an ergometer with respect to the performance supplied by a user depending on time and/or distance.

Known memory units for controlling an ergometer are integrated into the ergometer electronics and only allow different programs to be stored and recalled.

OBJECTS AND SUMMARY OF THE INVENTION

A principal object of the invention is to expand the training possibilities offered by an ergometer controlled by a program. Another object of the present invention is to provide an ergometer programmed to make the training more interesting.

For example, it is possible to store the complete data in the memory unit during the course of the program by providing the memory unit as an independent structural element. In this manner the stored data may be used at another time, even under different conditions and at a different location, to control an ergometer in accordance with the stored data. Furthermore, with a memory unit of this type, it is a simple matter to conduct an exercise session. Accordingly, it is possible to recall the most recent base data as comparison values and to compare the value obtained after exercise with the original values to even obtain new base values.

Another advantage of the memory unit of the present invention is the rapid programming of code memories. If, for example, a plurality of ergometers are provided in an exercise studio, the program required for a given user that has been stored in the memory unit in the first testing exercise, can be stored using a special code in the memories of all of the ergometers, thereby permitting the user to easily use any of the ergometers.

An additional significant advantage of the memory unit according to the present invention is that it can be used with a bicycle computer to store programs that characterize the journey performed with the bicycle. These journeys can then be simulated on an ergometer with the aid of the memory unit. This characteristic is also advantageous for competitive cyclists because they can experience the competition on the track. With the data obtained, the cyclist can utilize the ergometer to enhance the training program to this track in an optimal manner.

The memory unit according to the present invention advantageously includes a plug contact device for easy connection to an ergometer or to a bicycle computer.

In one preferred embodiment, the memory unit plug contact device is a cylindrical plug. If the memory unit also has a corresponding cylindrical shape, then it can be arranged in the plug at a very low cost and yet possess a relatively large memory capacity.

It is advantageous for the memory unit to contain an EEPROM, enabling stored data to be erased without difficulty. Additionally, the memory unit preferably also includes a ROM, a RAM, a pulse generator, and a real-time clock, all of which are connected to a microcontroller, which is also included in the memory unit. The memory unit can then access all data without difficulty, even from a bicycle computer which includes a number of sensors, especially sensors for the rotational speed of the pedals, the selected gear in the transmission, the slope of the travel path in the direction of travel, and for the pulse of the cyclist.

BRIEF DESCRIPTION OF THE DRAWINGS

The present invention is described in greater detail below with the aid of an exemplary embodiment illustrated in the drawings.

DETAILED DESCRIPTION OF THE PREFERRED EMBODIMENTS

Figure 1:
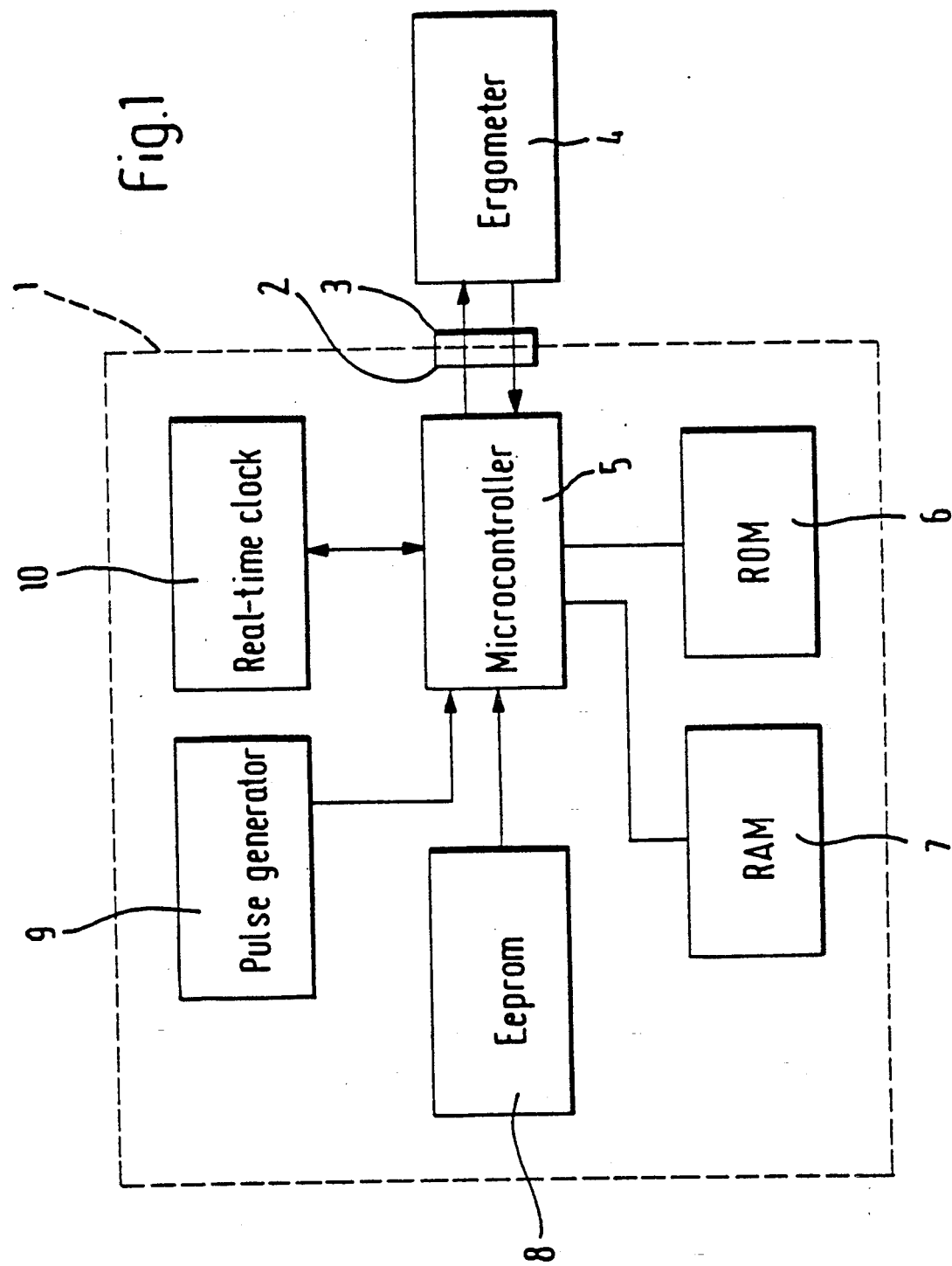
FIG. 1 is a block circuit diagram of an exemplary embodiment of the memory unit of the present invention in combination with an ergometer.

Referring now to FIG. 1, memory unit 1 is shown as an independent structural unit having a cylindrical plug 2, which can be inserted into a corresponding socket 3, of an ergometer 4. Ergometer 4 is formed in a known manner and therefore has a conventional electronic control (not shown), which contains a microprocessor. The plug connection formed by the plug 2 and the socket 3 thus represents an in series break point between the control of the ergometer 4 and the memory unit 1. The memory unit 1 has a cylindrical shape adapted to the diameter of the plug 2. It can therefore be connected directly to the plug 2 or be partially placed therein. A surrounding cover for the memory unit 1 and the plug 2 provides a shield against static, mechanical and magnetic forces, and also makes the entire unit extremely water-tight.

As shown in FIG. 1, the memory unit 1 includes a micro-controller 5 to which a ROM 6, a RAM 7, an EEPROM 8, a pulse generator 9, and a real time clock 10 are operatively connected. The memory unit 1 is thus in a position to store all data delivered from the ergometer 4 according to the program, and on the basis of the stored data the time and/or distance performance to be accomplished by the user of the ergometer 4 can be provided to the ergometer 4.

Figure 2:
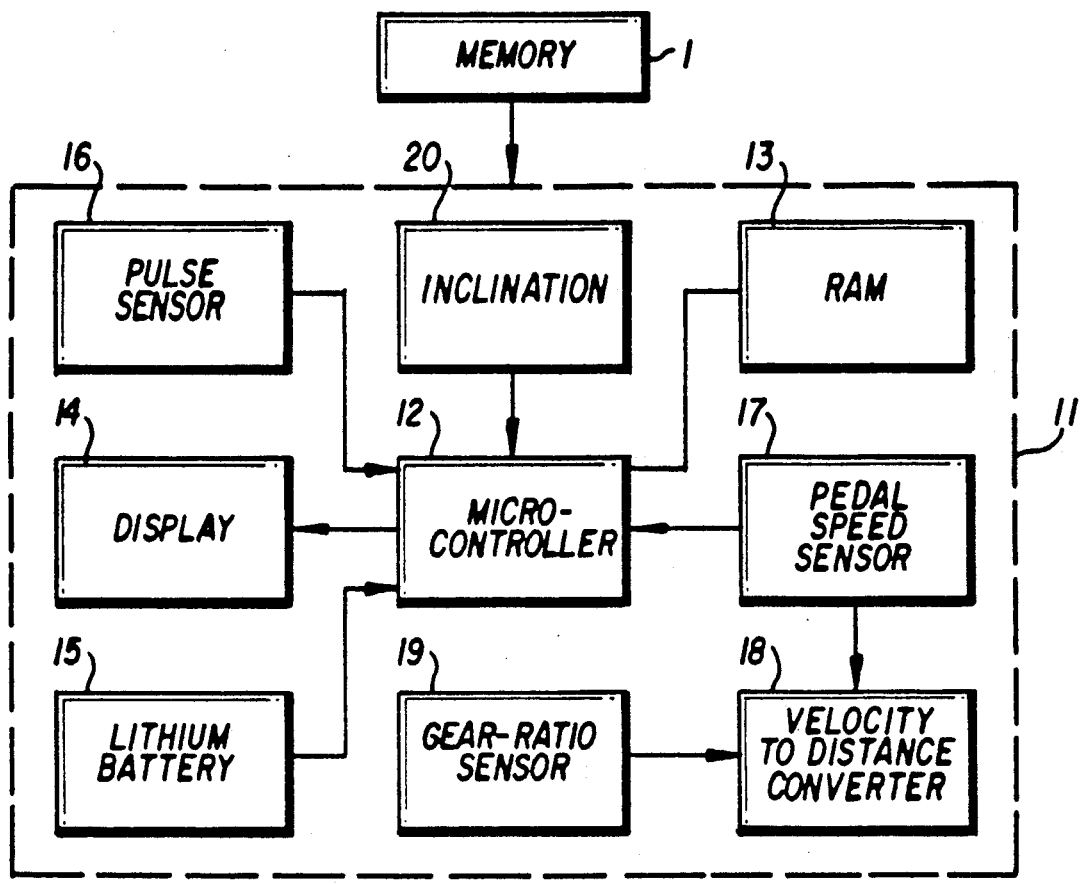
FIG. 2 is the exemplary embodiment of the memory unit according to FIG. 1, in combination with a bicycle computer, as shown in block circuit diagram.
Figure 3:
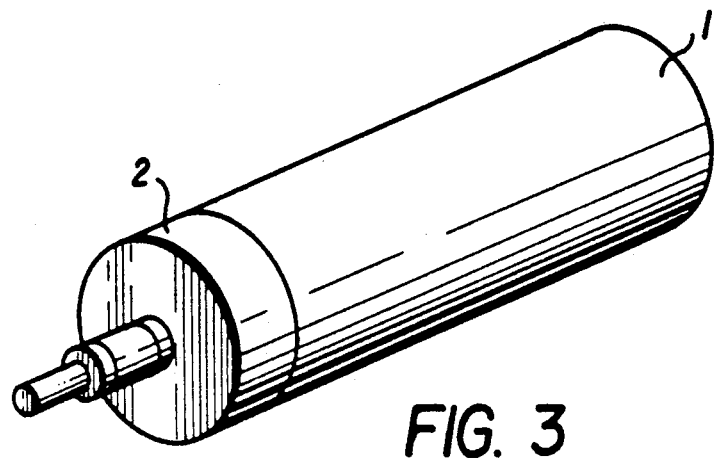
FIG. 3 is a perspective view of the memory unit and cylindrical plug.

The data delivered by a bicycle computer 11 can also be stored in the memory unit 1 and can be delivered to an ergometer on call. This is true even when the bicycle computer 11 contains a micro-controller 12 to which the memory unit 1 is connected. As shown in FIG. 2, in addition to the micro-controller 12, the bicycle computer 11, includes a RAM 13, a display 14, and a battery 15 (preferably of the lithium type), all of which are connected to the micro-controller 12. A pulse sensor 16, an inclination sensor 20 which recognizes the slope of the travel path in the direction, traveled and a pedal rotational speed recognizing sensor 17, are also all connected to the micro-controller 12. The pedal speed sensor or tachometer 17 is connected to a velocity/distance converter 18, which performs the speed and distance calculations. An additional gear ratio sensor 19 which recognizes the selected gear in the transmission is connected to the converter 18 to yield appropriate velocity and distance values.

Although only preferred embodiments are specifically illustrated and described herein, it will be appreciated that many modifications and variations of the present invention are possible in light of the above teachings and within the purview of the appended claims without departing from the spirit and intended scope of the invention.

What is claimed is:

1. Memory unit for use with an ergometer, comprising:
   a) means for controlling said ergometer with respect to a performance applied by a user in dependence on time and/or distance;
   b) means for removably connecting said memory unit to said ergometer; and
   c) means for data storage for a period of time until subsequent recall. including a ROM, a RAM, a pulse generator, and a real time clock, each of which are connected to a micro-controller;
   wherein the memory unit is selectively connectable with said ergometer and with a bicycle computer.

2. The memory unit according to claim 1, wherein said connecting means includes a plug contact device for connection to said ergometer.

3. The memory unit according to claim 2, wherein said plug contact device is a cylindrical plug.

4. The memory unit according to claim 3, having a cylindrical shape.

5. The memory unit according to claim 4, further including an EEPROM.

6. The memory unit according to claim 3, wherein said memory unit cylindrical shape is adapted to that of the cylindrical plug.

7. The memory unit according to claim 6, further including an EEPROM.

8. The memory unit according to claim 3, further including and EEPROM.

9. The memory unit according to claim 2, having a cylindrical shape.

10. The memory unit according to claim 9, further including an EEPROM.

11. The memory unit according to claim 2, further including an EEPROM.

12. The memory unit according to claim 1, having a cylindrical shape.

13. The memory unit according to claim 12, wherein said memory unit cylindrical shape is adapted to that of the cylindrical plug.

14. The memory unit according to claim 12, further including an EEPROM.

15. The memory unit according to claim 1, further including an EEPROM.

16. The memory unit according to claim 1, wherein said bicycle computer is mounted on a bicycle and said bicycle includes rotatable pedals, a transmission having gears providing gear ratios, said bicycle is adapted for travel over differing slopes and in selectable directions, and said bicycle computer includes sensors for the rotational speed of the pedals, the selected gear of the transmission, and the slope of the travel path in the direction of travel, as well as a micro-controller to which the sensors, a RAM and an interface with the memory unit are connected.

17. The memory unit according to claim 16, wherein the bicycle computer has a pulse sensor connected to the micro-controller.

18. The memory unit according to claim 1, wherein the bicycle computer contains a display that is connected to the micro-controller.

19. The memory unit according to claim 18, wherein the bicycle computer has a pulse sensor connected to the micro-controller.

20. Apparatus for recording as data ergometric values generated by traversal of a given course by a rider on a pedal-driven bicycle, comprising:
   a) a microcontroller;
   b) a pulse sensor connected to said microcontroller;
   c) an inclination sensor connected to said microcontroller;
   d) means for storage of digital data, connected to said microcontroller;
   e) means for sensing pedal rotation rate and for generating therefrom a velocity value; and
   f) means for converting said velocity values to velocity/distance values.

21. The apparatus of claim 20, further including means connected to said microcontroller for displaying said values.

22. The apparatus as in claim 20 wherein said bicycle includes means for changing the gear ratio applied by the pedals, further including means for supplying gear ratio values to said means for converting.

23. The apparatus as in claim 20, further including means for storage and recall of said values.

24. The apparatus of claim 23, further including plug connection means, wherein said storage and recall means is detachable from said apparatus for recording by said plug connection means.

25. A memory unit for storage and recall of ergometric data values, comprising:
   a) a microcontroller;
   b) a pulse generator connected to said microcontroller;
   c) a real-time clock connected to said microcontroller;
   d) volatile memory means connected to said microcontroller for temporary data storage;
   e) non-volatile memory means connected to said microcontroller for program storage; and
   f) erasable memory means for storage of said data values.

26. The apparatus as in claim 25, further including connection means for detachably connecting said memory storage unit to an ergometer.

27. The memory unit according to claim 26, wherein said connection means includes a plug contact device for connection to said ergometer.

28. A system for recording as data the ergometric values generated by traversal of a given course by a rider on a bicycle, and for recall of the ergometric data values generated by such traversal, comprising:
   a) a bicycle computer having:
      i) a bicycle computer microcontroller;
      ii) a pulse sensor connected to said bicycle computer microcontroller;
      iii) an inclination sensor connected to said bicycle computer microcontroller;
      iv) means for storage of digital data, connected to said bicycle computer microcontroller;
      v) means for sensing pedal rotation rate and for generating therefrom a velocity value; and
      vi) means for converting said velocity values to velocity/distance values;
   b) a memory unit for recallably storing ergometric data values, comprising:
      i) a memory unit microcontroller;
      ii) a pulse generator connected to said memory unit microcontroller;
      iii) a real-time clock connected to said memory unit microcontroller;

iv) volatile memory means connected to said memory unit microcontroller for temporary data storage;
v) non-volatile memory means connected to said memory unit microcontroller for program storage; and
vi) erasable memory means for storage of said data values; and
c) an ergometer.

* * * * *